United States Patent [19]

Fu et al.

[11] Patent Number: 5,814,628
[45] Date of Patent: Sep. 29, 1998

[54] BENZYL-SUBSTITUTED COMPOUNDS HAVING DOPAMINE RECEPTOR AFFINITY

[75] Inventors: Jian-Min Fu, Brampton; Ashok Tehim, Mississauga; Robert A. Kirby, Acton, all of Canada

[73] Assignee: Allelix Biopharmaceuticals Inc., Mississauga, Canada

[21] Appl. No.: 762,984

[22] Filed: Dec. 10, 1996

Related U.S. Application Data

[62] Division of Ser. No. 354,766, Dec. 12, 1994, Pat. No. 5,602,120.
[51] Int. Cl.$^6$ ........................ C07D 401/14; C07D 403/14; A61K 31/55
[52] U.S. Cl. .............................. 514/220; 540/557
[58] Field of Search ............................ 540/557; 514/220

[56] References Cited

U.S. PATENT DOCUMENTS

| | | | |
|---|---|---|---|
| 3,539,573 | 11/1970 | Schmutz | 260/268 |
| 3,546,226 | 12/1970 | Schmutz | 260/268 |
| 3,751,415 | 8/1973 | Schmutz | 260/268 |
| 3,758,479 | 9/1973 | Schmutz | 260/268 |
| 3,761,481 | 9/1973 | Nakanishi et al. | 540/551 |
| 3,884,922 | 5/1975 | Nakanishi et al. | 540/551 |
| 3,908,010 | 9/1975 | Schmutz | 424/250 |
| 3,983,234 | 9/1976 | Sayers | 424/250 |
| 4,096,261 | 6/1978 | Horrom | 424/250 |
| 5,354,747 | 10/1994 | Hansen | 514/211 |
| 5,538,965 | 7/1996 | Tehim et al. | 514/211 |

FOREIGN PATENT DOCUMENTS

| | | |
|---|---|---|
| 772160 | 11/1967 | Canada. |
| 0 003 016 | 7/1979 | European Pat. Off.. |
| 1290768 | 9/1972 | United Kingdom. |
| 95/17400 | 6/1995 | WIPO. |

OTHER PUBLICATIONS

Nielsen et al., *Jour. of Heterocyclic Chem.*, "Annulated 1,2,3–Triazols 3[1]Synthesis of 1,2,3–Triazolo[4,5,b][1,5]benzoxazepin–10(9H)–ones and 10–(4–Substituted–1–piperazinyl)–1,2,3–triazolo[4,5–b][1,5]benzoxazepines", 22, No. 6, 1693–1701 (1985).

Jilek et al., *Collection of Czechoslovak Chemical Communications*, "Potential Neuroleptics; N–Aralkyl, N–(Aroylalkyl) and N–Pyridyl Derivatives of 10–Piperazino–10, 11–Dihydrodibenzo[b,f]Thiepins", 40, 3386–3398 (1975).

Gianai et al Synthesis, 1985, p. 550 "A new facile synthesis of 11–oxo–10, 11–dihydro–5H–dibenzo[b,e][1,4]diazepines".

Harris et al. J. Med Chem, 1982, 25:855 "Affinity of 10–(4–methylpiperazino)dibenz[b,f]oxepins for clozapine and spiroperidol binding sites in rat brain".

Klunder et al J Med Chem, 1992, 35:1887 "Novel non-–nucleoside inhibitors of HIV–1 reverse transcriptase. tricyclic pyridobenzoxazepinones and dibenzoxazepinones".

de Paulis et al J. Med Chem, 1981, 24(9):1021 "Synthesis of clozapine analogues and their affinity for clozapine and spiroperidol binding sites in rat brain".

Sindelar et al Coll. Czechoslov. Chem. Commun., 1977, 42:2231 Noncataleptic potential neuroleptics: 2–nitro and 2–hydroxy derivatives of 10–(4–methylpiperzino)–10, 11–dihydrodibenzo[b,f]thiepin.

*Primary Examiner*—Emily Bernhardt
*Attorney, Agent, or Firm*—Nikaido Marmelstein Murray & Oram LLP

[57] ABSTRACT

Described herein are D4 receptor-selective compounds of the general formula:

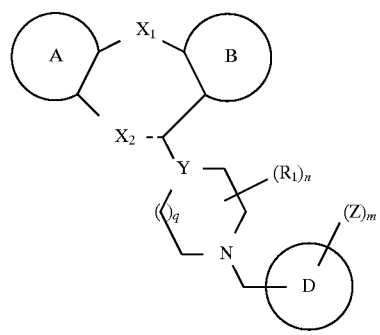

wherein:

A and B are independently selected, optionally substituted, saturated or unsaturated 5- or 6-membered, homo- or heterocyclic rings;

$X_1$ is selected from $CH_2$, O, NH, S, C=O, CH—OH, CH—N($C_{1-4}$alkyl)$_2$, C=CHCl, C=CHCN, N—$C_{1-4}$alkyl, N-acetyl, $SO_2$ and SO;

$X_2$—is selected from N=, $CH_2$—, CH=, C(O)—, O—, and S—;

Y is selected from CH and N;

Z is cyano $R_1$ represents $C_{1-4}$alkyl;

m is 0, 1, 2 or 3;

n is 0, 1 or 2;

q is 1 or 2; and

D is a 5, 6 or 7-membered, saturated or unsaturated, homo- or heterocyclic ring; and acid addition salts, solvates and hydrates thereof. Their use as ligands for dopamine receptor identification and in a drug screening program, and as pharmaceuticals to treat indications in which the D4 receptor is implicated, such as schizophrenia, is also described.

11 Claims, No Drawings

BENZYL-SUBSTITUTED COMPOUNDS HAVING DOPAMINE RECEPTOR AFFINITY

This is a division of application Ser. No. 08/354,766 filed Dec. 12, 1994. now U.S. Pat. No. 5,602,120.

The invention relates to compounds that bind to the dopamine D4 receptor, to their preparation and their use for therapeutic and drug screening purposes.

BACKGROUND TO THE INVENTION

Neuronal cell receptors that bind the neurotransmitter dopamine constitute a group of at least five structurally distinct proteins that can now be produced using recombinant DNA techniques. These techniques have been applied to construct cell lines that incorporate the dopamine receptor in their membranes, to provide regenerable and homogeneous substrates with which chemical libraries can be screened to identify potential CNS-active drugs.

Recent evidence strongly implicates the dopamine receptor classified as D4 in the etiology of schizophrenia. It has been suggested that compounds capable of interfering with the function of this receptor, which is present in schizophrenics at levels that are six times normal, would be useful in the treatment of this disease (Seeman et al, Nature, 1993, 365:441). Some drugs currently on the market in fact exhibit the desired antagonism of D4 receptor activity, and bind with relative strong affinity to the receptor. Yet because of their structure, these drugs interact also with related dopamine receptors, particularly the D2 receptor type, which results in significant side effects that include altered motor function and tachycardia. It would be desirable to provide compounds that exhibit not only a high degree of affinity for the D4 receptor, but also a relatively low degree of affinity for the D2 receptor. In this specification, this desired combination of receptor binding properties is referred to as D4 selectivity.

Products currently marketed to treat indications in which the D4 receptor function is implicated include the, dibenzodiazepine, clozapine, and the dibenzoxazepine, isoloxapine. Analysis of their dopamine receptor binding properties has shown that the preference for binding the D4 receptor relative to the D2 receptor is about 10 fold, for both products. Similarly, both bind the D4 receptor with about the same affinity (Ki value approximately 20 nM). Other products, recently published in the scientific literature, have shown similar D4 to D2 selectivity profile and D4 affinity values.

It is an object of the present invention to provide a compound having an improved D4 selectivity profile.

It is another object of the present invention to provide a compound having an improved D4 binding affinity.

It is another object of the present invention to provide a compound having both an improved D4 selectivity profile and D4 binding affinity.

It is a further object of the present invention to provide a pharmaceutical composition comprising a compound of the present invention, as active ingredient.

SUMMARY OF THE INVENTION

According to one aspect of the present invention, there is provide a compound of Formula I:

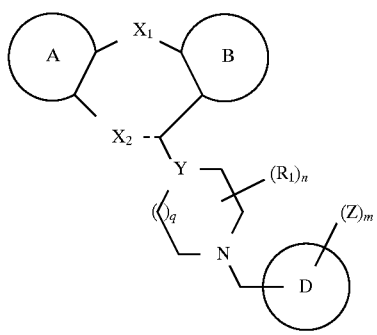

wherein:

A and B are independently selected, optionally substituted, saturated or unsaturated 5- or 6-membered, homo- or heterocyclic rings;

$X_1$ is selected from $CH_2$, O, NH, S, C=O, CH—OH, CH—N($C_{1-4}$alkyl)$_2$, C=CHCl, C=CHCN, N-$C_{1-4}$alkyl, N-acetyl, $SO_2$ and SO;

$X_2$—is selected from N=, $CH_2$—, CH=, C(O)—, O—, and S—;

Y is selected from CH and N;

Z is cyano $R_1$ represents $C_{1-4}$alkyl;

m is 0, 1, 2 or 3;

n is 0, 1 or 2;

q is 1 or 2; and

D is a 5, 6 or 7-membered, saturated or unsaturated, homo- or heterocyclic ring; and acid addition salts, solvates and hydrates thereof; with the proviso that when m is 0 then $X_1$, $X_2$—, A and B are selected to form the tricycle 8-chlorodibenz[b,f][1,4]oxazepine; and when $X_2$—is $CH_2$, ring D is benzene, m is 1 and Y is cyano at the para position, then $X_1$ is not $CH_2$.

According to another aspect of the invention, there is provided a pharmaceutical composition comprising a compound of Formula I and a pharmaceutically acceptable carrier.

In a further aspect of the invention, there is provided an analytical method in which a compound of the invention is used either to distinguish the D4 receptor from other receptor types or from the D2 receptor.

These and other aspects of the present invention are now described in greater detail hereinbelow.

DETAILED DESCRIPTION AND PREFERRED EMBODIMENTS

The invention relates to compounds that bind the dopamine D4 receptor in a selective manner, relative to the dopamine D2 receptor. It has been found, more particularly, that the D4 selectivity of D4-binding ligands having the tricyclic structure:

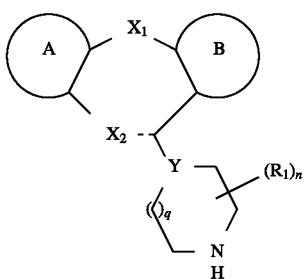

is significantly improved when the piperazine group is derivatized by a function having the structure:

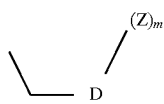

In accordance with one of its aspects, the present invention accordingly provides compounds that conform to Formula I:

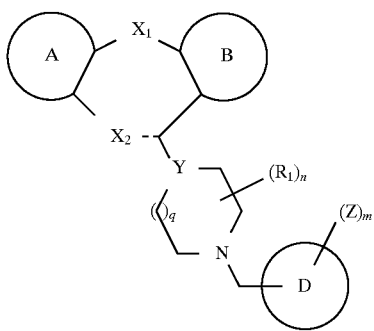

In embodiments of the invention, the ring D is a 5, 6 or 7-membered, saturated or unsaturated, homo- or heterocyclic ring that is optionally substituted by 1, 2 or 3 cyano groups. Particular embodiments of the invention include those in which ring D is a five membered ring such as cyclopentane, cyclopentene, furan, thiophene, pyrrole, pyrrolidine, imidazole, pyrazole, triazole, thiazole, and oxazole. In another embodiment ring D is a six membered ring such as cyclohexane, piperidine, benzene, pyridine, pyrazine, pyridazine, pyrimidine, triazine, pyran, morpholine and thiomorpholine. In a particular embodiment of the invention, ring D is benzene optionally substituted with 1, 2 or 3 cyano groups at the ortho, meta or para positions. In specific embodiments of the invention, ring D is benzene or benzene substituted by cyano at any one of the ortho, meta or para positions.

The tricyclic function to which ring D is coupled can have various structures and will typically incorporate those found to be important for dopamine D4 receptor binding. In other words, the tricycles suitable for coupling to ring D are those which, when substituted by functions other than ring D, are determined by the assay herein described, to bind the D4 receptor (preferably the human D4 receptor) with an affinity not greater than 1 μM (Ki). In particular, the rings A and B are selected, according to embodiments of the invention, from benzene, pyridine, pyrimidine, pyrazine, pyridazine, pyrole, imidazole, triazole, pyrazole, thiophene, thiazole, and pyran. In a particular embodiment, ring A is selected from benzene and pyridine and ring B is selected from benzene, pyridine, pyrimidine, pyrazine, pyridazine, pyrole, imidazole, triazole, pyrazole, thiophene, thiazole, furan and pyran; and is particularly selected from benzene and pyridine. In specific embodiments of the invention, both rings A and B are benzene. It is to be appreciated that when rings A and B are heterocycles, the heteroatoms are shared with the central seven membered ring only when the shared heteroatom is N. Such tricycles are within the scope of the Formula I; one embodiment of which is described by Lednicer et al in *The Organic Chemistry of Drug Synthesis*, (1992, John Wiley & Sons Inc., New York) wherein ring B is imidazole that is fused to a thiazepine at one of the imidazole nitrogen atoms.

One or both rings A and B may be substituted with from 1 to 3, usually 1 or 2, substituents. When substituted, the substituents are selected from hydroxyl, halo, $C_{1-4}$alkyl, amino, nitro, cyano, halo-substituted $C_{1-4}$alkyl, $C_{1-4}$alkoxy, halo-substituted $C_{1-4}$alkoxy, $C_{1-4}$alkoxycarbonyl, $C_{1-4}$acyl, halo-substituted $C_{1-4}$acyl, cyclo-$C_{3-7}$alkyl, thio-$C_{1-4}$alkylene, $C_{1-4}$alkylthio, halo-substituted $C_{1-4}$alkylthio, cyanothio, tetrazolyl, N-piperidinyl, N-piperazinyl, N-morpholinyl, acetamido, $C_{1-4}$alkylsulfonyl, halosulfonyl, halo-substituted $C_{1-4}$alkylsulfonyl, $C_{1-4}$alkylsulfoxyl, sulfonamido, $C_{1-4}$alkylseleno, and $OSO_3H$.

Substitution sites on rings A and B will be limited in practice to the carbon atoms on the ring that are not shared with the central seven membered ring. For example, a benzene ring can accomodate up to 4 substituents; pyridine, and pyran rings can accomodate up to 3 substituents; pyrimidine, pyrazine, pyridazine, pyrole, furan and thiophene rings can accomodate up to 2 substituents; imidazole, pyrazole and thiazole rings can accomodate only 1 substituent; and a triazole ring can accomodate no substituents. It is also to be understood that rings A and B may incorporate substituents at nitrogen atoms on the ring that are not shared with the central seven membered ring. For example the NH member of an imidazole ring may be substituted. In particular embodiments, rings A and B are substituted with from 1 to 2 substituents selected from chloro, fluoro, methyl, trifluoromethyl, methoxy, nitro, cyano and methylthio. In particularly preferred embodiments ring A is benzene substituted with 1 or 2 substituents selected from chloro, methyl, nitro and cyano and ring B is benzene substituted with 1 or 2 substituents selected from chloro, methoxy, trifluoromethyl and nitro.

In the central, 7-membered ring of the tricycle, $X_1$ may be any one of $CH_2$, O, NH, S, C=O, CH—OH, CH—N($C_{1-4}$alkyl)$_2$, C=CHCl, C=CHCN, N—$C_{1-4}$alkyl, N-acetyl, $SO_2$ and SO, while $X_2$— may be any one of N=, $CH_2$—, CH=, C(O)—, O—, and S—. In a particular embodiment of the invention, $X_1$ is O, S or NH. In another embodiment, $X_2$— is N= or CH=. In a particularly preferred embodiment, $X_1$ is O, S or NH and $X_2$— is N= or CH=. In specific embodiments $X_1$ and $X_2$— are selected to form a seven membered ring selected from oxazepine, diazepine, thiazepine and thiepine.

In preferred embodiments $X_1$ and $X_2$—together with rings A and B are selected to form a tricycle that is selected from 5H-dibenzo[b,e][1,4]diazepine that is optionally substituted, for example with one of 7,8-dichloro, 7,8-dimethyl, 2-chloro, 3-chloro, 4-chloro, 2,4-dichloro, 4,7,8-trichloro, 2-trifluoromethyl, 1-fluoro, or 2-methoxy; dibenz[b,f][1,4]oxazepine that is optionally substituted, for example with one of 4-nitro, 8-chloro, 4-cyano or 4-chloro; dibenzo[b,f]thiepine that is optionally substituted, for example with one of 2-nitro or 2-chloro; 11H-dibenzo[b,f]thiepine that is optionally substituted, for example with 2-methylthio; and dibenzo[b,f][1,4]thiazepine that is optionally substituted, for example with 8-chloro. In a specific embodiment of the invention, $X_1$ and $X_2$—together with rings A and B are selected to form a tricycle that is selected from:
dibenz[b,f][1,4]oxazepine; and
8-chlorodibenz[b,f][1,4]oxazepine.

In a most preferred embodiment, $X_1$ and $X_2$—together with rings A and B form a tricycle that is 8-chlorodibenz[b,f][1,4] oxazepine.

In an embodiment of the invention, the N-containing ring coupled to the tricyclic structure may incorporate 0, 1 or 2 $R_1$ substituents that are $C_{1-4}$alkyl groups, such as methyl. The piperazinyl ring may incorporate an additional $CH_2$ group (q=2) to form a diazepine ring as described by Horrom et al (U.S. Pat. No. 4,096,261). In another embodiment of the invention, Y is N thereby forming a piperazine or imidazolidine ring or Y is CH thereby forming a pyrrolidine or piperidine ring, depending on the value of q. In particular embodiments of the invention, n is 0; q is 1 and Y is N. In a specific embodiment n, q and Y are chosen to give an unsubstituted piperazinyl ring.

In a particular embodiment of the invention, there are provided compounds of formula (I) exhibiting better D4 selectivity than clozapine, including:
8-chloro-11-(4-benzyl-1-piperazinyl)-dibenz[b,f][1,4] oxazepine;
11-[4-(2-cyanobenzyl)-1-piperazinyl]dibenz[b,f][1,4] oxazepine;
11-[4-(3-cyanobenzyl)-1-piperazinyl]dibenz[b,f][1,4] oxazepine; and
11-[4-(4-cyanobenzyl)-1-piperazinyl]dibenz[b,f][1,4] oxazepine.

In a more preferred embodiment, there are provided compounds of formula (I) exhibiting better D4 affinity and selectivity than clozapine, including:
8-chloro-11-(4-benzyl-1-piperazinyl)-dibenz[b,f][1,4] oxazepine.

Acid addition salts of the compound of Formula I include for example those formed with inorganic acids e.g. hydrochloric, sulphuric or phosphoric acids and organic acids e.g. succinic, maleic, acetic or fumaric acid. Other non-pharmaceutically acceptable salts e.g. oxalates may be used for example in the isolation of compounds of Formula I for ligand use, or for subsequent conversion to a pharmaceutically acceptable acid addition salt. Also included within the scope of the invention are solvates and hydrates of the invention.

The conversion of a given compound salt to a desired compound salt is achieved by applying standard techniques, in which an aqueous solution of the given salt is treated with a solution of base e.g. sodium carbonate or potassium hydroxide, to liberate the free base which is then extracted into an appropriate solvent, such as ether. The free base is then separated from the aqueous portion, dried, and treated with the requisite acid to give the desired salt.

It will be appreciated that certain compounds of Formula I may contain an asymmetric centre. Such compounds will exist as two (or more) optical isomers (enantiomers). Both the pure enantiomers and the racemic mixtures (50% of each enantiomer), as well as unequal mixtures of the two, are included within the scope of the present invention. Further, all diastereomeric forms possible (pure enantiomers and mixtures thereof) are within the scope of the invention.

The compounds of the present invention can be prepared by processes analogous to those known in the art. The present invention therefore provides, in a further aspects, a process for the preparation of a compound of Formula I or a salt, solvate or hydrate thereof, which comprises the step of coupling a reagent of Formula A:

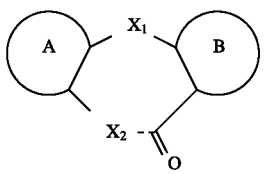

a reagent of Formula B:

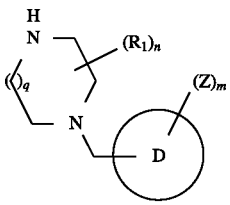

using a Lewis acid such as $TiCl_4$ or $BF_3.Et_2O$.

Reagent (A) can be obtained commercially or can be synthesized using established ring closure procedures. For example, when $X_1$ is NH and $X_2$—is N= (a diazepine), reagent (A) may be prepared according to the procedures described by Giani et al (Synthesis, 1985, 550) by refluxing equimolar amounts of 2-chlorobenzoic acid, o-phenylenediamine and powdered copper in chlorobenzene. The following is a schematic representation of the reaction to obtain the diazepine form of reagent (A):

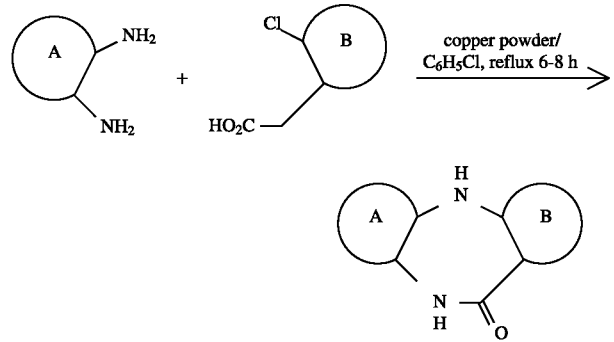

When $X_1$ is O and $X_2$—is N=(an oxazepine), reagent (A) may be prepared according to the procedures described by Klunder (J. Med. Chem. 1992, 35:1887) by condensation of a 2-aminophenol with 2-chloro-5-nitrobenzoyl chloride in THF to afford the corresponding carboxamide followed by refluxing with NaOH for ring closure. The following is a schematic representation of the steps to obtain the oxazepine form of reagent (A):

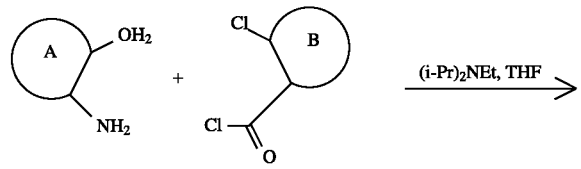

-continued

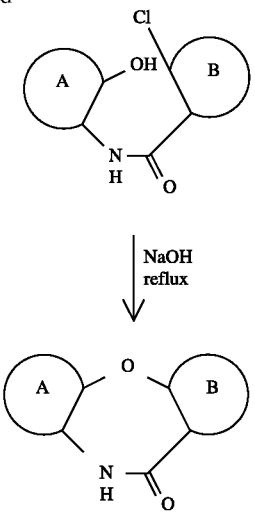

The thiepine form of reagent (A), i.e. when $X_1$ is S and $X_2$—is CH=, may be prepared according to the procedures described by Sindelar et al (Collect. Czech. Chem. Commun, 1983, 48(4):1187). When reagent (A) is an oxepine i.e. when $X_1$ is O and $X_2$—is $CH_2$—, it may be prepared in the manner reported by Harris et al (J. Med. Chem., 1982, 25(7):855); and the corresponding cycloheptene reagent (A) i.e. when $X_1$ and $X_2$—are both $CH_2$, may be prepared as reported by De Paulis et al (J. Med. Chem. 1981, 24(9):1021). The thiazepine reagent (A) may be prepared in a four step process starting from 1-bromo-2-nitrobenzene and methyl thiosalicylate. The steps involve coupling; reduction of the nitro group; hydrolysis of the ester group; and finally ring closure.

Many of the reagents of Formula B are similarly available from various commercial sources. In the alternative, or where the desired reagent is not commercially available, reagent B can be synthesized from the corresponding 1-piperazinecarboxyaldehyde by reaction with Halo—$CH_2$—D, where halo is desirably the bromo derivative. Halo—$CH_2$— substituted ring D compounds are commercially available such as benzyl bromide and α-bromotolunitrile or may be synthesized using established synthetic techniques.

In the specific case where Y=CH, synthesis proceeds by coupling isonicotinic acid (4-benzyl derivative thereof) with an amino reagent of the formula:

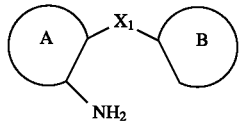

using a suitable coupling agent such as EDCI, to form an amide intermediate. The amino reagent may be obtained commercially or may be synthesized according to established synthetic techniques. For example, 2-chloronitrobenzene can be converted to the amino reagent 2-aminodiphenylsulphide (or oxide) by substitution with thiobenzene (or hydroxybenzene) in the presence of $K_2CO_3$ and then reducing in the presence of Zn. The resulting amide intermediate can then be cyclized with a suitable ring closure agent such as $POCl_3$ to give the final compound according to formula I wherein Y is CH.

For use as a ligand, the present compounds can be stored in packaged form for reconstitution and use. The compounds can be used to distinguish dopamine receptors from other receptor types, for example glutamate and opioid receptors, within a population of receptors and in particular to distinguish between the D4 and D2 receptors. The latter can be achieved by incubating preparations of the D4 receptor and of the D2 receptor with a D4 selective compound of the invention and then incubating the resulting preparation with a radiolabelled dopamine receptor ligand, such as $^3$H-spiperone. The D2 and D4 receptors are then distinguished by determining the difference in membrane-bound radioactivity, with the D4 receptor exhibiting lesser radioactivity, i.e., lesser $^3$H-spiperone binding.

In another embodiment of the invention, the compound is provided in labelled form, such as radiolabelled form e.g. labelled by incorporation within its structure of $^3$H or $^{14}$C or by conjugation to $^{125}$I. Such radiolabelled forms can be used to directly to distinguish between dopamine D4 and dopamine D2 receptors. Furthermore, radiolabelled forms of the present compounds can be exploited to screen for more potent dopamine D4 ligands, by determining the ability of the test ligand to displace the radiolabelled compound of the present invention.

The clozapine-like binding profile of the present compounds indicates their utility as pharmaceuticals that may be useful for the treatment of various conditions in which the use of a dopamine D4 receptor ligand is indicated, such as for the treatment of anxiety and schizophrenia.

For use in medicine, the compounds of the present invention are usually administered in a standard pharmaceutical composition. The present invention therefore provides, in a further aspect, pharmaceutical compositions comprising an effective amount of a compound of Formula I or a pharmaceutically acceptable salt, solvate or hydrate thereof and a pharmaceutically acceptable carrier.

The compounds of the present invention may be administered by an convenient route, for example by oral, parenteral, buccal, sublingual, nasal, rectal or transdermal administration and the pharmaceutical compositions formulated accordingly.

The compounds and their pharmaceutically acceptable salts which are active when given orally can be formulated as liquids, for example syrups, suspensions or emulsions, tablets, capsules and lozenges.

A liquid formulation will generally consist of a suspension or solution of the compound or pharmaceutically acceptable salt in a suitable pharmaceutical liquid carrier for example, ethanol, glycerine, non-aqueous solvent, for example polyethylene glycol, oils, or water with a suspending agent, preservative, flavouring or colouring agent.

A composition in the form of a tablet can be prepared using any suitable pharmaceutical carrier routinely used for preparing solid formulations. Examples of such carriers include magnesium stearate, starch, lactose, sucrose and cellulose.

A composition in the form of a capsule can be prepared using routine encapsulation procedures. For example, pellets containing the active ingredient can be prepared using standard carriers and then filled into hard gelatin capsule; alternatively, a dispersion or suspension can be prepared using any suitable pharmaceutical carrier, for example aqueous gums, celluloses, silicates or oils and the dispersion or suspension filled into a soft gelatin capsule.

Typical parenteral compositions consist of a solution or suspension of the compound or pharmaceutically acceptable salt in a sterile aqueous carrier or parenterally acceptable oil, for example polyethylene glycol, polyvinyl pyrrolidone, lecithin, arachis oil or sesame oil. Alternatively, the solution can be lyophilized and then reconstituted with a suitable solvent just prior to administration.

Compositions for nasal administration may conveniently be formulated as aerosols, drops, gels and powders. Aerosol formulations typically comprise a solution or fine suspension of the active substance in a physiologically acceptable aqueous or non-aqueous solvent and are usually presented in single or multidose quantities in sterile form in a sealed container, which can take the form of a cartridge or refill for use with an atomising device. Alternatively, the sealed container may be a unitary dispensing device such as a single dose nasal inhaler or an aerosol dispenser fitted with a metering valve which is intended for disposal after use. Where the dosage form comprises an aerosol dispenser, it will contain a propellant which can be a compressed gas such as compressed air or an organic propellant such as flurochlorohydrocarbon.

The aerosol dosage forms can also take the form of a pump-atomizer.

Compositions suitable for buccal or sublingual administration include tablets, lozenges, and pastilles, wherein the active ingredient is formulated with a carrier such as sugar, acacia, tragacanth, or gelatin and glycerine.

Compositions for rectal administration are conveniently in the form of suppositories containing a conventional suppository base such as cocoa butter.

Preferably, the composition is in unit dose form such as a tablet, capsule or ampoule. Suitable unit doses i.e. therapeutically effective amounts; can be determined during clinical trials designed appropriately for each of the conditions for which administration of a chosen compound is indicated and will of course vary depending on the desired clinical endpoint. It is anticipated that dosage sizes appropriate for administering the compounds of the examples will be roughly equivalent to, or slightly less than, those used currently for clozapine. Accordingly, each dosage unit for oral administration may contain from 1 to about 500 mg and will be administered in a frequency appropriate for initial and maintenance treatments.

EXAMPLE 1

8-Chloro-11-(4-benzyl-1-piperazinyl)-dibenz[b,f][1, 4]oxazepine

The starting material 8-chloro-10,11-dihydro-dibenz[b,f] [1,4]oxazepin-11-one was prepared according to the procedures reported in Coyne et al (J. Med. Chem., 1967, 10:541). Briefly, this entailed coupling potassium salicylaldehyde with 2,5-dichloronitrobenzene, followed by oxidation to carboxylic acid, reduction of nitro, and finally ring closure, to yield the desired 8-chloro starting material.

To a stirred solution of 8-chloro-10,11-dihydro-dibenz[b, f][1,4]oxazepin-11-one (0.3 g; 1.22 mmol) in dry toluene (10 mL) at room temperature was added 1-benzyl piperazine (1.0 mL; 5.61 mmol; Aldrich) followed by the dropwise addition of $TiCl_4$ (1M in toluene, 1.47 mL; 1.47 mmol). The reaction mixture was refluxed for 2 hours, cooled to room temperature and then poured into an ammonium hydroxide solution (30%, 50 mL). The resulting mixture was extracted with dichloromethane (4×50 mL), and the combined organic phases were then dried ($K_2CO_3$) and concentrated. Purification of the product was conducted on silica gel using ethyl acetate:hexane (5:1→4:1) as the eluant to give 0.471 g (95%) of the title compound as a yellow solid; m.p. 50°–52° C.

The hydrochloride salt of the title compound was subsequently prepared by dissolving the base (0.1 g ; 0.227 mmol) in 1 mL of 3N-HCl in ethyl acetate, then stirring at room temperature for 15 minutes. The solution was removed under vacuum and the resulting oil was triturated with dry methanol (5 mL). The solvent was evaporated under reduced pressure to yield 0.110 g (quantitative) of the hydrochloride salt, as a pale yellow solid; m.p. 172°–174° C. (decomp.).

EXAMPLE 2

11-[4-(2-cyanobenzyl)-1-piperazinyl]dibenz[b,f][1, 4]oxazepine

To a stirred solution of 11-(1-piperazinyl)dibenz[b,f][1,4] oxazepine (2.79 g, 10.0 mmol) (prepared from 10,11-dihydrodebenz[b,f][1,4]oxazepine-11-one, Aldrich and piperazine, as in example 1) in DMF (25 mL) was added sodium hydride (0.56 g, 60% in oil, 14 mmol) at 0° C. under argon. The mixture was stirred at 0° C. for 10 minutes at room temperature for 20 minutes, and then treated with β-bromo-o-tolunitrile (2.35 g, 12.0 mmol, Aldrich). The resulting mixture was stirred at room temperature overnight and quenched with saturated ammonium chloride solution (25 mL). The mixture was separated and extracted with ethyl acetate (3×50 mL). The combined organic phase was dried over magnesium sulfate and filtered. The filtrate was concentrated in vacuo to dryness and the residue was subjected to column chromatography using ethyl acetate:hexane (1:2) as the eluent. The title compound was obtained as a white solid (2.34 g, 59%), m.p. 136°–138° C.; MS 395 ($M^+$+1).

In a like manner, there was prepared the following additional compounds:

11-[4-(3-cyanobenzyl)-1-piperazinyl]dibenz[b,f][1,4] oxazepine, 51%, m.p. 154°–156° C.; MS 395 ($M^+$+1) from 11-(1-piperazinyl)dibenz[b,f][1,4]oxazepine; and 11-[4-(4-cyanobenzyl)-1-piperazinyl]dibenz[b,f][1,4] oxazepine, 57%, m.p. 166°–168° C.; MS 395 ($M^+$+1) from 11-(1-piperazinyl)dibenz[b,f][1,4]oxazepine.

Also in a like manner, there is prepared the 8-chloro substituted equivalents 8-chloro11-[4-(2-cyanobenzyl)-1-piperazinyl]dibenz[b,f][1,4]oxazepine; 8-chloro-11-[4-(3-cyano benzyl)-1-piperazinyl]dibenz[b,f][1,4]oxazepine; and 8-chloro-11-[4-(4-cyanobenzyl)-1-piperazinyl]dibenz[b,f] [1,4]oxazepine from8-chloro-11-(1-piperazinyl)dibenz[b,f] [1,4] oxazepine.

EXAMPLE 3

Receptor Binding Assay

D2 and D4 receptor-binding affinities of the compounds of examples 1 and 2 were evaluated according to their ability to reduce binding of $^3$H-spiperone as compared to the reference compound clozapine. The potency of the test compound to reduce $^3$H-spiperone binding directly correlated to its binding affinity for the receptor.

D4 Receptor Preparation

HEK 298 (human embryonic kidney) cells stably transfected with human D4 receptor (D4.2 sub-type) were grown in NUNC cell factories for 5 days (75% confluency) without a media change and removed with versene (approximately 19 mg of cells per cell factory tray). The cells were then centrifuged in a Sorval centrifuge for 10 minutes, 5000 rpm (GS3 rotor) and the pellets quickly frozen in liquid nitrogen and stored at –80° C. until used in binding assay. When used in the assay, cells were thawed on ice for 20 minutes and then 10 mL of incubation buffer (50 mM Tris, 1 mM EDTA, 4 mM $MgCl_2$, 5 mM KCl, 1.5 mM $CaCl_2$, 120 mM NaCl, pH7.4) was added. The cells were then vortexed to resuspend pellet and homogenized with a Kinematica CH-6010 Kriens-LU homogenizer for 15 seconds at setting 7. Concentration of receptor protein was determined using the Pierce BCA assay.

D2 Receptor Preparation $GH_4C_1$ (rat pituitary) cells stably transfected with the human D2 receptor (short isoform) were grown in $CO_2$ independent media in roller bottles (1500 cm$^2$) for 10 days. 100 $\mu$M $ZnSO_4$ was added to the cells (the D2 promoter being zinc inducible). After 16 hours, fresh media was added to allow the cells to recover for 24 hours. The cells were harvested using versene and then centrifuged in a Sorval centrifuge for 10 minutes, at 5000 rpm (GS3 rotor). Pellets were quickly frozen in liquid nitrogen and stored at –80° C. until used in the binding assays. When used in the assay, cells were thawed on ice for 20 minutes. Each roller bottle produced approximately 72 mg of protein. 10 mL of incubation buffer was added to the pellets which were then vortexed, resuspended and homogenized with a Kinematica CH-6010 Kriens-LU homogenizer for 15 seconds at setting 7. The receptor protein concentration was determined using the Pierce BCA assay.

Total Spiperone Binding Assay

The incubation was started by the addition of 500 $\mu$l (50 $\mu$g protein) membrane homogenate to a solution of 900 $\mu$l incubation buffer and 100 $\mu$l (0.25 nM final conc.) $^3$H-spiperone (90 Ci/mmol Amersham diluted in borosilicate glass vial) in 12×75 mm polypropylene tubes. The tubes were vortexed and incubated at room temperature for 90 minutes. The binding reaction was stopped by filtering using a Brandell Cell Harvester. The samples were filtered under vacuum over glass fibre filters (Whatman GF/B) presoaked for 2 hours in 0.3% polyethylenimine (PEI) in 50 mM Tris buffer (pH7.4). The filters were then washed 3 times with 5 mL ice cold 50 mM Tris buffer (pH7.4). Individual filter disks were put in scintillation vials (Bioivals, Bechman). Ready Protein Plus liquid scintillant (5 mL, Beckman) was added and the vials counted by liquid scintillation spectrophotometry (Beckman LSC 6500) after equilibrating for three hours at room temperature to determine total binding ($B_T$)

Non-Specific Binding Assay for D4

The incubation was started by the addition of 500 $\mu$l (50 $\mu$g protein) membrane homogenate to a solution of 400 $\mu$l incubation buffer, 100 $\mu$l $^3$H-spiperone (90 Ci/mmol Amersham diluted in borosilicate glass vial to 0.25 nM final conc.) and 500 $\mu$l (30 $\mu$M final conc.) of fresh dopamine (Research Biochemicals Inc., light protected and dissolved in incubation buffer) in 12×75 mm polypropylene tubes. The tubes were vortexed and incubated at room temperature for 90 minutes at which time the binding reaction was stopped by filtering. The filters were washed and counted using the same procedure as in the total binding assay described above to give the non-specific binding value (NSB).

Non-Specific Binding Assay for D2

This assay employed the same procedures as the non-specific binding assay for D4 with the exception that 2 $\mu$M (final conc.) of (–) sulpiride (Research Chemicals Inc.) was used in place of dopamine.

Displacement Binding Assay

The incubation was started by the addition to 12×75 mm polypropylene tubes 500 $\mu$l (50 $\mu$g protein) membrane homogenate to a solution of 400 $\mu$l incubation buffer, 100 $\mu$l (0.25 final conc.) $^3$H-spiperone (90Ci/mmol, Amersham, diluted in borosilicate glass vial to) and 500 $\mu$l of test compound that was prepared from 1 mM stock dissolved in DMSO and stored at –20° C. in polypropylene cryogenic storage vials until dilution in incubation buffer in borosilicate glass vials. The tubes were vortexed and incubated at room temperature for 90 minutes at which time the binding reaction was stopped by filtering. The filters were washed and counted using the same procedure as in the total binding assay described above to give the displacement binding value ($B_D$).

Calculations

The test compounds were initially assayed at 1 and 0.1 $\mu$M and then at a range of concentrations chosen such that the middle dose would cause about 50% inhibition of $^3$H-spiperone binding. Specific binding in the absence of test compound ($B_0$) was the difference of total binding ($B_T$) minus non-specific binding (NSB) and similarly specific binding (in the presence of test compound) (B) was the difference of displacement binding ($B_D$) minus non-specific binding (NSB). $IC_{50}$ was determined from an inhibition response curve, logit-log plot of %B/$B_0$ vs concentration of test compound.

Ki was calculated by the Cheng and Prustoff transformation:

$Ki=IC_{50}/(1+[L]/K_D)$ where [L] is the concentration of $^3$H-spiperone used in the assay and $K_D$ is the dissociation constant of $^3$H-spiperone determined independently under the same binding conditions.

Assay results are reported in the following Table:

| COMPOUND | STRUCTURE | Ki | D2/D4 |
|---|---|---|---|
| clozapine | 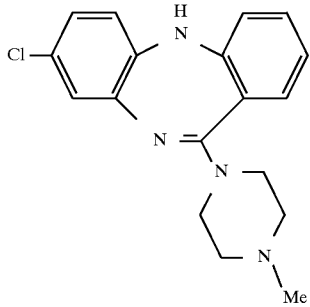 | 23 | 10 |
| 8-chloro-11-(4-benzyl-1-piperazinyl)dibenz[b,f][1,4]oxazepine | 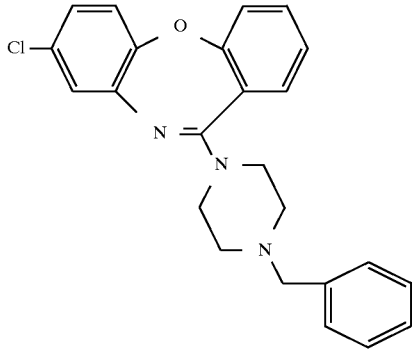 | 19 | 31.7 |
| 11-[4-(2-cyanobenzyl)-1-piperazinyl]dibenz[b,f][1,4]oxazepine | 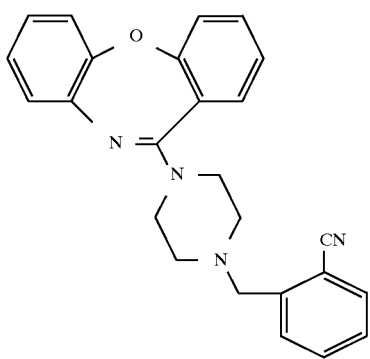 | 519 | 16.1 |
| 11-[4-(3-cyanobenzyl)-1-piperazinyl]dibenz[b,f][1,4]oxazepine | 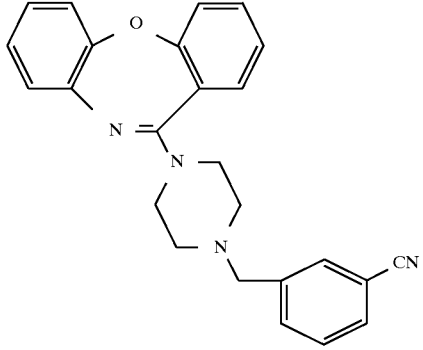 | 134 | 21.7 |
D4 AFFINITY AND SELECTIVITY -continued

D4 AFFINITY AND SELECTIVITY

| COMPOUND | STRUCTURE | Ki | D2/D4 |
|---|---|---|---|
| 11-[4-(4-cyanobenzyl)-1-piperazinyl]dibenz[b,f][1,4]oxazepine | 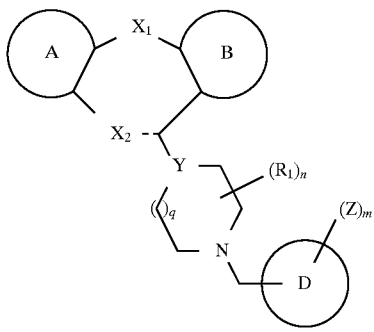 | 108 | 90.1 |

We claim:

1. The compound of Formula 1:

wherein:

A and B are benzene unsubstituted or substituted with 1–3 substituents selected independently from hydroxyl, halo, $C_{1-4}$alkyl, amino, nitro, cyano, halo-substituted $C_{1-4}$alkyl, $C_{1-4}$alkoxy, halo-substituted $C_{1-4}$alkoxy, $C_{1-4}$alkoxycarbonyl, $C_{1-4}$acyl, cyclo-$C_{3-7}$alkyl, thiol-$C_{1-4}$alkylene, $C_{1-4}$alkylthio, halo-substituted $C_{1-4}$alkylthio, cyanothio, tetrazolyl, N-piperidinyl, N-piperazinyl, N-morpholinyl, acetamido, $C_{1-4}$alkylsulfonyl, halosulfonyl, halo-substituted $C_{1-4}$alkylsulfonyl, $C_{1-4}$alkylSO—, sulfonamido, $C_{1-4}$alkylseleno, and $OSO_3H$;

$X_1$ is selected from NH, N—$C_{1-4}$alkyl, and N-acetyl;
$X_2$—is N=;
Y is selected from CH and N;
Z is cyano;
$R_1$ represents $C_{1-4}$alkyl;
m is 1, 2 or 3;
n is 0, 1 or 2;
q is 1 or 2; and
D is benzene; and acid addition salts or hydrates thereof.

2. The compound according to claim 1, wherein A is selected from benzene and B is selected from benzen wherein A and B are independently unsubstituted or substituted with 1 or 2 substituents selected independently from hydroxyl, halo, $C_{1-4}$alkyl, amino, nitro, cyano, halo-substituted $C_{1-4}$alkyl, $C_{1-4}$alkoxy, halo-substituted $C_{1-4}$-alkoxy, $C_{1-4}$alkoxycarbonyl, $C_{1-4}$acyl, cyclo-$C_{3-7}$alkyl, thiol-$C_{1-4}$alkylene, $C_{1-4}$alkylthio, halo-substituted $C_{1-4}$alkylthio, cyanothio, tetrazolyl, N-piperidinyl, N-piperazinyl, N-morpholinyl, acetamido, $C_{1-4}$alkylsulfonyl, halosulfonyl, halo-substituted $C_{1-4}$alkylsulfonyl, $C_{1-4}$alkylso-sulfonamido, $C_{1-4}$alkylseleno, and $OSO_3H$.

3. The compound according to claim 1, wherein A is benzene substituted by 1 or 2 substituents selected from chloro, methyl, methylthio, nitro and cyano.

4. The compound according to claim 1, wherein B is benzene substituted by 1 or 2 substituents selected from fluoro, chloro, trifluoromethyl, methoxy, nitro and cyano.

5. The compound according to claim 1, wherein $X_1$ is selected from NH.

6. The compound according to claim 1, wherein ring D is benzene and m is 1.

7. The compound according to claim 2, wherein ring D is benzene and m is 1.

8. The compound according to claim 3, wherein ring D is benzene and m is 1.

9. The compound according to claim 4, wherein ring D is benzene and m is 1.

10. The compound according to claim 5, wherein ring D is benzene and m is 1.

11. A pharmaceutical composition, comprising a therapeutically effective amount of a compound according to claim 1, and a pharmaceutically acceptable carrier.

* * * * *